United States Patent [19]
Bascos et al.

[11] Patent Number: 5,407,070
[45] Date of Patent: Apr. 18, 1995

[54] ONE-TIME RESEALABLE PACKAGE FOR NEEDLED MEDICAL DEVICES

[76] Inventors: Christine M. Bascos, 16039 Tacoma, Detroit, Mich. 48205; Santiago A. Bascos, 9365 Pollock, Selinas, Calif. 93907

[21] Appl. No.: 108,995
[22] Filed: Aug. 18, 1993
[51] Int. Cl.6 ............... B65D 83/10; B65D 73/00
[52] U.S. Cl. .................. 206/365; 206/364; 206/467
[58] Field of Search ............ 206/364, 365, 367, 467, 206/140

[56] References Cited

U.S. PATENT DOCUMENTS

| | | | |
|---|---|---|---|
| 2,887,215 | 5/1959 | Hutchinson | 206/365 |
| 3,353,664 | 11/1967 | Armentrout et al. | 206/365 |
| 3,473,646 | 10/1969 | Burke | 206/571 |
| 4,106,621 | 8/1978 | Sorenson | 206/365 |
| 4,300,682 | 11/1981 | Kuchenbecker | 206/467 |
| 4,415,084 | 11/1983 | Hauser et al. | 206/467 |
| 4,860,943 | 8/1989 | Cooper | 206/140 |
| 4,921,096 | 5/1990 | McFarlane | 206/349 |
| 4,979,616 | 12/1990 | Clanton | 206/364 |
| 5,031,768 | 7/1991 | Fischer | 206/370 |
| 5,133,454 | 7/1992 | Hammer | 206/364 |
| 5,154,293 | 10/1992 | Gould | 206/467 |
| 5,156,267 | 10/1992 | Yates, Jr. et al. | 206/364 |

*Primary Examiner*—Paul T. Sewell
*Assistant Examiner*—Marie Denise Patterson
*Attorney, Agent, or Firm*—Marshall & Melhorn

[57] ABSTRACT

A one-time resealable package for needled medical devices, composed generally of a stiff plastic body which has a predetermined shape for receiving the needled medical device and is provided with a perimeter lip, and further composed of a flexible backing layer which is sealably secured to the perimeter lip, wherein a first portion of the backing layer is releasably secured to the perimeter lip while a second portion of the baking layer is permanently secured to the perimeter lip. The first portion of the backing layer is connected to an arrow-shaped end portion having a pair of opposed barbs. The perimeter lip is provided with an aperture adjacent the arrow-shaped end portion, wherein the arrow-shaped end portion is insertable thereinto. Preferably, the body is at least in part form fitting with respect to the needled medical device so as to abuttably interact with the needled medical device so that the needle thereof cannot contact the body when the needled medical device is received within the body. In operation, a user peels the backing layer from the body until the permanently secured portion thereof is encountered to access the needled medical device. Upon completion of its usage, the needled medical device is replaced into the body, and the user then manipulates the arrow-shaped end portion so that it is lockably forced into the aperture in the peripheral lip to thereby permanently entomb the needled medical device within the package.

7 Claims, 1 Drawing Sheet

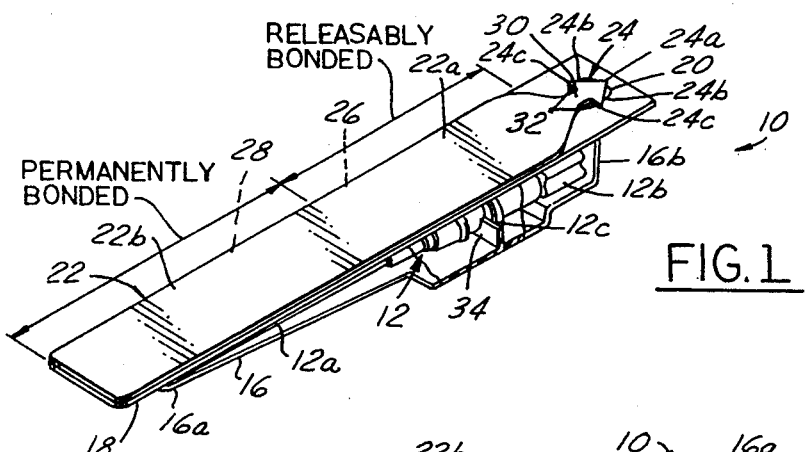
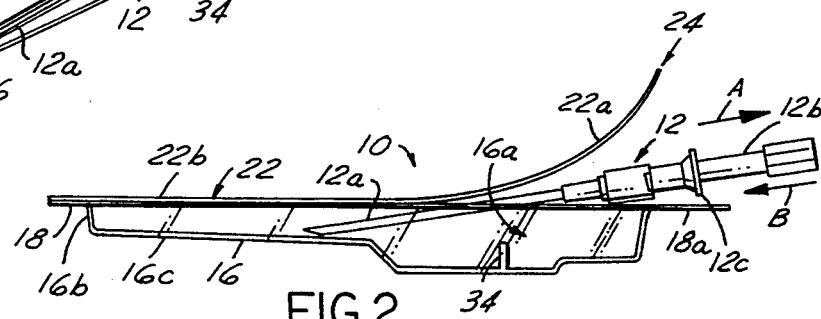
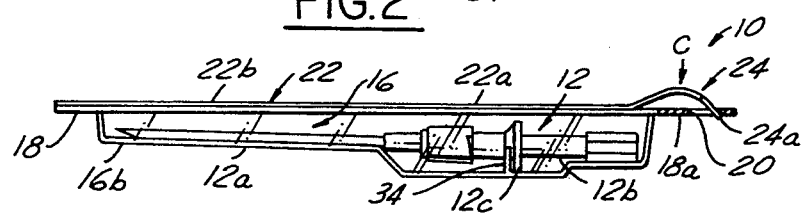
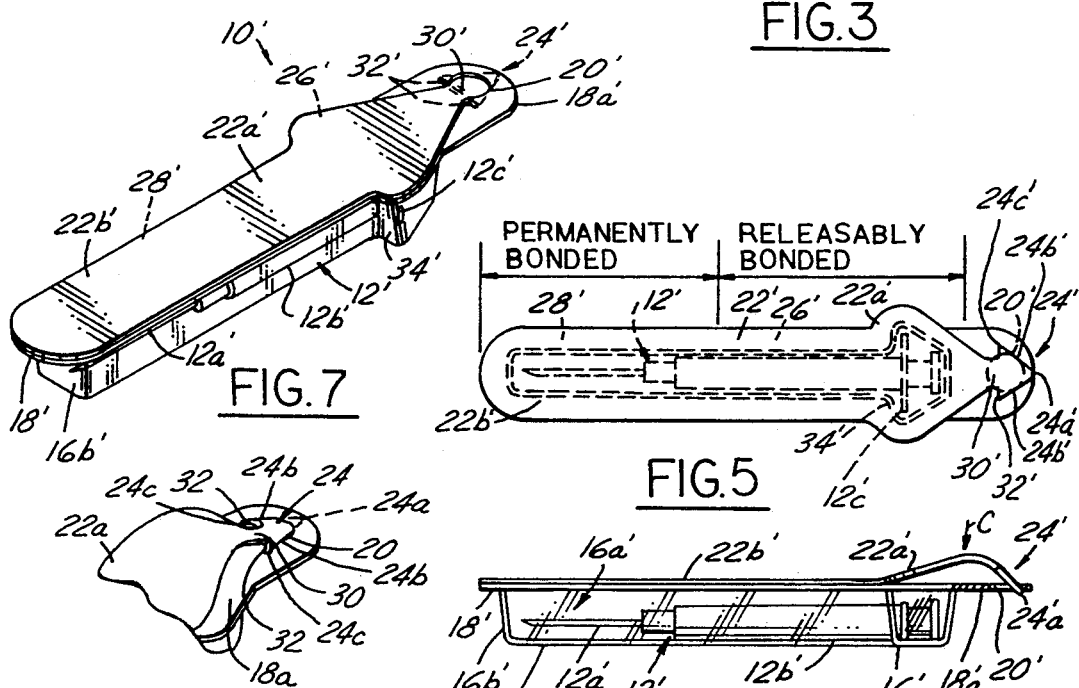
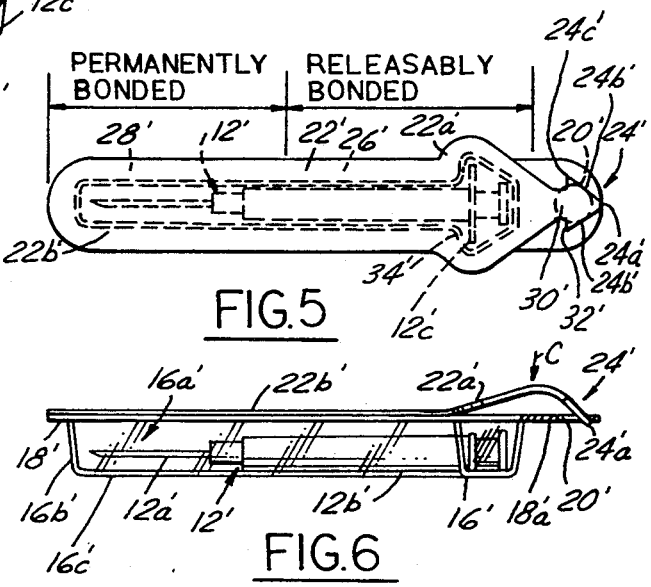

ONE-TIME RESEALABLE PACKAGE FOR NEEDLED MEDICAL DEVICES

BACKGROUND OF THE INVENTION

1. Field of the Invention

The present invention relates to packaging for needled medical devices, such as needled syringes, needled catheters and needle assemblies, wherein hazardous bio-medical contamination is generally involved with their usage. More particularly, the present invention relates to resealable packaging for needled medical devices. Still more particularly, the present invention relates to such packaging in the form of a one-time resealable packaging that is inexpensive, safe and easy to use and affords reliable protection for medical personnel handling bio-medically contaminated needles.

2. Description of the Prior Art

Handling of needles is a well known hazard for medical personnel because needled medical devices, such as disposable needled syringes, disposable needled catheters and needle assemblies used for syringes and for catheters, may easily subject the medical worker to puncture wounds, especially when being removed from its package or while being disposed of. Disposal procedures can involve a particularly increased risk of puncture wounding when a protective cap must be snap fit over the needle of the needled medical device. It is also well known that bio-medical hazard, such as for instance HIV and HBV, is associated with used needled medical devices, which may subject medical personnel handling disposal of the needled medical device to disease and/or an expensive and painful treatment regimen.

Accordingly, there is immense need in the health care industry for packaging for needled medical devices which reduces puncture wound hazard. U.S. Pat. No. 3,473,646 to Burke, dated Apr. 12, 1968, discloses a syringe assembly contained in a blister-type, peel open package having a see through plastic housing and a peelably attached heavy paper backing. U.S. Pat. No. 4,921,096 to McFarlane, dated May 1, 1990, discloses a package for needled medical devices having a mutually separable, two segment upper end for permitting the needled medical instrument to be removed from the package and then replaced and resealed therein; a shrink wrap is provided to ensure sterility. U.S. Pat. No. 4,979,616 to Clanton, dated Dec. 25, 1990, discloses a box-shaped receptacle having a top panel and a bottom panel in which tabs and seats mutually engage to encapsulate the syringe. U.S. Pat. No. 5,031,768 to Fischer, dated Jul. 16, 1991, discloses a hinged tray for holding medical instruments, including disposable syringes, which inhibits contamination of sterile instruments and affords a safe disposal container by being permanently locked by operation of notched posts. U.S. Pat. No. 5,133,454 to Hammer, dated Jul. 28, 1992, discloses a needles and catheter container having a hinged top panel carrying brackets to hold the needle and catheter, wherein the top is opened and resealed by operation of detents that are releasable by a user pressing upon a handle. Finally, U.S. Pat. No. 5,156,267 to Yates, Jr. et al, dated Oct. 20, 1992, discloses a two part hinged syringe container which is resealable via protuberances on one part being forced into depressed indentations on the other part.

While the above described devices attempt to address the problem of needled medical device disposal, they lack cost effectiveness, simplicity of manufacture and ease of operation. Accordingly, what remains needed is a package for needled medical devices which affords simplicity of manufacture, cost effectiveness, assurance of sterility, easy and safe opening and resealing of the package in conjunction with safe handling of the needled medical device, and assured, permanent lockage of the package once it has been resealed.

SUMMARY OF THE INVENTION

The present invention is a package for needled medical devices which affords simplicity of manufacture, cost effectiveness, assurance of sterility, easy and safe opening and resealing of the package in conjunction with safe handling of the needled medical device, and assured, permanent lockage of the package once it has been resealed.

The one-time resealable package according to the present invention is composed generally of a stiff plastic body which has a predetermined shape for receiving the needled medical device and further is provided with a perimeter lip, and is composed further of a flexible backing layer which is sealably secured to the perimeter lip, wherein a first portion of the backing layer is releasably secured with respect to the perimeter lip while a second portion of the backing layer is permanently secured to the perimeter lip. The first portion of the backing layer is connected with an arrow-shaped end portion having a pair of opposed barbs. The perimeter lip is provided with an aperture adjacent the arrow-shaped end portion, wherein the arrow-shaped end portion is insertable thereinto. Preferably, the body is at least in part form fitting with respect to the needled medical device so as to abuttably interact with the needled medical device so that the needle thereof cannot contact the body when the needled medical device is received within the body.

In operation, a user grasps the arrow-shaped end portion in one hand and the body in the other hand and thereupon effects to peel the backing layer from the body until the permanently secured portion thereof is encountered. The user then carefully removes the needled medical device from the package. The user then utilizes the needled medical device. Upon completion of this usage, the needled medical device is replaced into the body. The user then manipulates the arrow-shaped end portion so that the pointed end thereof enters the aperture in the peripheral lip of the body. The user then further manipulates the arrow-shaped end portion so that it is forced entirely through the aperture. The aperture is sized to provide an interference fit with barbs of the arrow-shaped end portion to thereby prevent the arrow-shaped end portion from being separated from the aperture. In this regard, the arrow-shaped portion is curlably bent as it is forced through the aperture by the user, and then resiliently assumes its original flat configuration upon passing through the aperture.

Accordingly, it is an object of the present invention to provide a one-time resealable package for needled medical devices.

It is another object of the present invention to provide a one-time resealable package for needled medical devices, wherein the package is sterile before being opened.

It is a further object of the present invention to provide a one-time resealable package for needled medical devices, wherein one-time resealing is afforded by an arrow-shaped end portion of a backing layer interferingly engaging with respect to an aperture in a body, the body being permanently attached to the backing layer at a portion thereof remote from the arrow-shaped end portion.

It is an additional object of the present invention to provide a one-time resealable package for needled medical devices, wherein the body thereof is provided with a predetermined shape which abuttingly interfaces with the needled medical device to prevent the needle thereof from contacting the body, and thereby obviate need for a needle cap.

It is yet a further object of the present invention to provide a one-time resealable package for needled medical devices which is simply constructed, inexpensive, provides assured sterility before being opened, provides easy and safe opening and resealing of the package in conjunction with safe handling of the needled medical device, and provides assured, permanent lockage of the package once it has been resealed.

BRIEF DESCRIPTION OF THE DRAWINGS

FIG. 1 is a perspective view of the one-time resealable package according to the present invention in operation with respect to a needled medical device in the form of a needled catheter.

FIG. 2 is a side view of the one-time resealable package depicted in FIG. 1, now shown in operation while the needled medical device is being either removed from or reinserted into the package.

FIG. 3 is a side view of the one-time resealable package depicted in FIG. 1 now being resealed so that the needled medical device will be entombed therewithin.

FIG. 4 is a detail, partly broken-away perspective view of the one-time resealable package according to the present invention, shown in operation wherein the arrow-shaped end portion of the backing layer is being curlably forced into the aperture of the body.

FIG. 5 is a top plan view of the one-time resealable package depicted in FIG. 5 now resealed with the needled medical device entombed therewithin.

FIG. 6 is a side view of the one-time resealable package depicted in FIG. 5, now shown in operation wherein the arrow-shaped end portion of the backing layer is being forced into the aperture of the body.

FIG. 7 is a perspective view of the one-time resealable package according to the present invention in operation with respect to a needled medical device in the form of a needled syringe.

DETAILED DESCRIPTION OF THE PREFERRED EMBODIMENT

Referring now to the Drawing, FIG. 1 generally depicts the one-time resealable package 10 according to the present invention, shown in operation encapsulating a needled medical device in the form of a needled catheter 12. It will be seen that the one-time resealable package 10 is composed generally of a body 16 having a peripheral lip 18 with an aperture 20 therein, and a flexible backing layer 22 sealably connected with the peripheral lip of the body for keeping the needled catheter 12 sterile. It will further be noted that the backing layer has an arrow-shaped end portion 24 located adjacent the aperture 20.

Now with reference being had additionally to FIG. 2 through 4, the structure and function of the one-time resealable package 10 will be detailed with greater specificity.

The body 16 is constructed of a durable, structurally strong material, preferably a stiff, see-through plastic formed by a vacuum forming process, such as for example a 0.020 to 0.030 inch thick Lexan or similar clear plastic. The body provides a body cavity 16a which is defined by a sidewall 16b and an integral bottom wall 16c. The body cavity 16a is shaped and sized to receive therein the needled catheter 12. The material of the body 16 is selected to provide resistance to puncturing by the needle 12a of the needled catheter 12, especially during placement of the needled catheter back into the body cavity 16a, as shown in FIG. 2. The peripheral lip 18 is located in a plane that is oriented generally perpendicular with respect to the sidewall 16b of the body 16. An end portion 18a of the peripheral lip 18 extends outwardly away from the body cavity 16a, and is provided with the aperture 20.

The backing layer 22 is composed of a flexibly stiff material, preferably a plastic sheet, such as for example cut out from 0.020 inch thick Lexan or similar plastic sheet. The backing layer 22 is shaped to overlay the peripheral lip 18. A first portion 22a of the backing layer 22 adjacent the arrow-shaped end portion 24 thereof is releasably bonded to the peripheral lip 18, such as by a peelably releasable adhesive 26. A second portion 22b of the backing layer opposite the arrow-shaped end portion 24 thereof is permanently bonded to the peripheral lip 18, such as by a permanent adhesive 28 or sonic welding. Preferably, the arrow-shaped end portion 24 is not bonded to the peripheral lip 18, so as to provide a readily graspable hand-hold for a user to grab when peeling the first portion 22a of the backing layer 22 from the peripheral lip 18.

The arrow-shaped end portion 24 is characterized by a point 24a defined by the convergence of a pair of leading edges 24b which terminate in a pair of opposed barbs 24c. The barbs 24c are connected with the first portion 22a of the backing layer 22 by a neck 30. Each barb 24c is defined by a barb edge 32 oriented preferably perpendicularly with respect to the neck 30. The aperture 20 has a cross-section which is less than the width of separation between the barbs 24c, but greater than the width of the neck 30. The neck 30 has a length which preferably locates the barb edges 32 at a part of the aperture 20 that is substantially closest the body cavity 16a.

In operation, a user holds the one-time resealable package 10 and grasps the arrow-shaped end portion 24 in one hand and the body 16 in the other hand and thereupon effects to peel the first portion 22a of the backing layer 22 from the peripheral lip 18 of the body 16 until the permanently secured second portion 22b of the backing layer is encountered. The user then carefully removes the needled catheter 12 from the body cavity 16a (see FIG. 2). The user then utilizes the needled catheter 12. Upon completion of this usage, the needled catheter 12 is replaced into the body cavity 16a (again see FIG. 2). The user then manipulates the arrow-shaped end portion 24 bendably as shown in FIG. 2 so that the pointed end 24a thereof enters the aperture 20 in the peripheral lip 18 of the body 16. The user then further manipulates the arrow-shaped end portion 24, such as by pressing down on the backing layer in the direction of arrow C, so that the leading edges 24b are forceably shoved entirely through the aperture 20 until the barbs 24c are trapped by the peripheral lip 18a at the other side of the aperture. The connection of the barbs 24c with the peripheral lip is preferably tight and without slack, and desirably, with some mutual biasing. Preferably in this As indicated, the cross-section of the aperture 20 is sized to provide an interference fit with respect to the separation of the barbs 24 so that the barb edges 32 interferingly abut the peripheral lip adjacent the aperture to thereby prevent the arrow-shaped end portion from being reversibly removed from the aperture. In this regard, the leading edges 24a will slidably about the aperture 20 in the manner of an inclined plane to thereby cause the arrow-shaped portion to curlably bend as it is forced through the aperture by the user. The material of the backing layer 22 while sufficiently flexible to permit the aforesaid curling, is yet structurally strong enough to prevent the barb edges 32 from deforming so as to permit the arrow-shaped end to back-out of the aperture once it has been seated interferingly with respect thereto. Further, the material of the backing layer is selected so that the arrow-shaped end portion 24 will resiliently assume its original flat configuration upon having passed through the aperture 20. As a consequence, the backing layer 22 is one-time resealed with respect to the body, thereby permanently entombing the used needled catheter 12 within the one-time resealable package 10, wherein its destruction is required to again gain access its contents.

In order to provide positional fixation of the needled catheter 12 relative to the body 16, the body is preferably provided with abutment surfaces 34 which are predetermined to abuttingly interface with a structural surface 12c of the non-needle portion 12b of the needled catheter 12. This abutting interface prevents the needle 12a from possibly abutting the sidewall 16a, so that a cap is not needed to envelop the needle 12a. As a result, cost savings can be expected with respect to conventional packaging, which generally must include a removable cap for the needle, as well as enhanced safety for the user, since there is no cap to replace upon the needle after the needled catheter 12 has been used.

While the foregoing discussion has centered upon a one-time resealable package 10 for a needled catheter 12, it is to be understood that the one-time resealable package according to the present invention can be used with any needled medical device. As a further preferred example, FIGS. 5 through 7 depict a one-time resealable package 10' shown being utilized with respect to a needled syringe 12'. Since the structure and function remains essentially as detailed hereinabove, the same numerals will be used to designate like functioning components, with a prime being added thereto. Accordingly, for the sake of brevity, the reader is requested to review FIGS. 5 through 7 in combination with a re-reading of the foregoing description for a complete understanding of the structure and function thereof keeping in mind that now a needled syringe 12' is being utilized instead of a needled catheter 12 exemplarly for the needled medical device. In this regard, FIG. 5 depicts an unopened, one-time resealable package 10' having a sterile body cavity 16b holding a needled syringe 12'; FIG. 6 shows the arrow-shaped end portion 24' being forced into the aperture 20' in order to (one-time) reseal the backing layer 22' with respect to the body 16'; and FIG. 7 shows the one-time resealable package 10' now resealed so as to permanently entomb the needled syringe 12' therewithin.

Operationally, the one-time resealable package 10' for a needled syringe 12' operates essentially as described hereinabove with respect to the needled catheter 12. One operational note, especially as relates to controlled substances that are kept under lock and key, is that after the user has removed the needled syringe 12' from the one-time resealable package 10' and has filled it with a prescribed amount with medication, the needled syringe may then be in part replaced into the one-time resealable package 10' in a manner analogous to that more-or-less depicted in FIG. 2, wherein the point of the needle 12a' is safely covered by the one-time resealable package. This obviates the need to cap the needle after the needled syringe has been filled (as would be necessary in conventional practice), since the needle is safely protected by the one-time resealable package 10' until used with respect to a patient. Thereafter, the needled syringe 12' is entombed, as described hereinabove, into the one-time resealable package 10', as shown in FIG. 7.

To those skilled in the art to which this invention appertains, the above described preferred embodiment may be subject to change or modification. For instance, the peelably releasable adhesive 26 may be selected to provided reactivated adhesion when the first portion 22a of the backing layer 22 is again resealed. Further for instance, other one-time connection devices that are structurally and functionally analogous to the herein described interaction between the arrow shaped end portion and the aperture can be used by those skilled in the art to effect resealing of the end portion of the backing layer to the end portion of the peripheral lip. Such change or modification can be carried out without departing from the scope of the invention, which is intended to be limited only by the scope of the appended claims.

What is claimed is:

1. A one-time resealable package for a needled medical device, comprising:

a body having a body cavity defined by a sidewall and a bottom wall integrally connected with said sidewall, said sidewall having a peripheral lip oriented in a plane generally perpendicular with respect to said sidewall, said peripheral lip having an end portion disposed exterior with respect to said body cavity;

a backing layer overlaying said peripheral lip, said backing layer terminating at one end in an end portion, said backing layer having a first portion connected with said end portion of said backing layer, said first portion being releasably bonded with said peripheral lip by a first peelably releasable adhesive, said backing layer having a second portion located opposite said end portion of said backing layer, said second portion being permanently bonded with said peripheral lip by a second, permanent adhesive, different from said first peelably releasable adhesive; and one-time connection means for permanently connecting said end portion of said backing layer with said end portion of said peripheral lip;

wherein the needled medical device is received in said body cavity and access thereto is provided by a user peeling said first portion of said backing layer from said peripheral lip; further wherein the needled medical device is replaced in said body cavity and then entombed therein by combination of said second portion being permanently bonded to a predetermined portion of said peripheral lip and the user using said one-time connection means to permanently connect said end portion of said backing layer with said end portion of said peripheral lip.

2. The one-time resealable package of claim 1, wherein said one-time connection means comprises:

said end portion of said peripheral lip having an aperture of a predetermined cross-section; and said end portion of said backing layer being an arrow shaped end portion located adjacent said aperture, said arrow-shaped end portion having a pair of opposed barbs, said pair of opposed barbs having a width of separation that exceeds said predetermined cross-section of said aperture;

wherein the needled medical device is entombed within said body cavity by the user forcing said arrow-shaped end portion through said aperture so that said pair of opposed barbs interferingly engages with respect to said peripheral lip located adjacent said aperture.

3. The one-time resealable package of claim 2, wherein said arrow-shaped end is characterized by a point defined by the convergence of a pair of leading edges which terminate in said pair of opposed barbs, said pair of opposed barbs being connected with said first portion of said backing layer by a neck having a neck width and a neck length, each barb of said pair of opposed barbs having a barb edge oriented substantially perpendicularly with respect to said neck, said predetermined cross-section of said aperture being greater than said neck width, said neck length being selected to locate each said barb edge abuttably against said peripheral lip adjacent said aperture when said arrow-shaped end portion has been forced through said aperture.

4. The one-time resealable package of claim 3, further comprising abutment means connected with said sidewall for interferingly abutting with the needled medical device received in said body cavity so that the needle thereof cannot strike against said sidewall.

5. A one-time resealable package for a needled medical device, comprising:

a body having a body cavity defined by a sidewall and a bottom wall integrally connected with said sidewall, said sidewall having a peripheral lip oriented in a plane generally perpendicular with respect to said sidewall, said peripheral lip having an end portion disposed exterior with respect to said body cavity, said end portion being provided with an aperture of a predetermined cross-section; and a backing layer overlaying said peripheral lip, said backing layer terminating at one end in an arrow-shaped end portion, said arrow shaped end portion being located adjacent said aperture, said arrow-shaped end portion having a pair of opposed barbs, said pair of opposed barbs having a width of separation that exceeds said predetermined cross-section of said aperture, said backing layer having a first portion connected with said arrow-shaped end portion, said first portion being releasably bonded with said peripheral lip by a first peelably releasable adhesive, said backing layer having a second portion located opposite said arrow-shaped end portion, said second portion being permanently bonded with said peripheral lip by a second, permanent adhesive, different from said first peelably releasably adhesive;

wherein the needled medical device is received in said body cavity and access thereto is provided by a user peeling said first portion of said backing layer from said peripheral lip; further wherein the needled medical device is replaced in said body cavity and then entombed therein by combination of said second portion being permanently bonded to a predetermined portion of said peripheral lip and the user forcing said arrow-shaped end portion through said aperture so that said pair of opposed barbs interferingly engages with respect to said peripheral lip located adjacent said aperture.

6. The one-time resealable package of claim 5, wherein said arrow-shaped end is characterized by a point defined by the convergence of a pair of leading edges which terminate in said pair of opposed barbs, said pair of opposed barbs being connected with said first portion of said backing layer by a neck having a neck width and a neck length, each barb of said pair of opposed barbs having a barb edge oriented substantially perpendicularly with respect to said neck, said predetermined cross-section of said aperture being greater than said neck width, said neck length being selected to locate each said barb edge abuttably against said peripheral lip adjacent said aperture when said arrow-shaped end portion has been forced through said aperture.

7. The one-time resealable package of claim 6, further comprising abutment means connected with said sidewall for interferingly abutting with the needled medical device received in said body cavity so that the needle thereof cannot strike against said sidewall.

* * * * *